United States Patent [19]

Tilles

[11] 4,341,702
[45] * Jul. 27, 1982

[54] HERBICIDAL ACTIVE SULFOXIDE AND SULFONE COMPOUNDS

[75] Inventor: Harry Tilles, El Cerrito, Calif.

[73] Assignee: Stauffer Chemical Company, Westport, Conn.

[ * ] Notice: The portion of the term of this patent subsequent to Nov. 10, 1998, has been disclaimed.

[21] Appl. No.: 219,618

[22] Filed: Dec. 24, 1980

Related U.S. Application Data

[63] Continuation of Ser. No. 567,910, Apr. 14, 1975, abandoned, which is a continuation-in-part of Ser. No. 371,325, Jun. 18, 1973, abandoned, which is a continuation-in-part of Ser. No. 280,385, Aug. 14, 1972, abandoned.

[51] Int. Cl.³ .............. C07D 211/34; C07D 215/08; C07D 223/06; C07D 295/20
[52] U.S. Cl. .................. 260/239 BF; 71/88; 71/94; 546/164; 546/245
[58] Field of Search ............... 260/239 BF; 546/245, 546/164

[56] References Cited

U.S. PATENT DOCUMENTS

| | | | |
|---|---|---|---|
| 3,066,020 | 11/1962 | Tilles | 546/245 |
| 3,124,447 | 3/1964 | Wineman et al. | 71/103 |
| 3,198,786 | 8/1965 | Tilles et al. | 260/239 BF |
| 3,579,525 | 5/1971 | Tilles et al. | 260/294.8 F |
| 3,598,859 | 8/1971 | Yates et al. | 71/103 |
| 3,639,404 | 2/1972 | Richter et al. | 260/283 S |
| 3,816,436 | 6/1974 | Walker | 260/294.8 F |
| 3,879,455 | 4/1975 | Tilles | 260/551 R |
| 3,936,458 | 2/1976 | Sturm et al. | 260/283 S |
| 3,989,684 | 11/1976 | Tilles | 260/239 A |

FOREIGN PATENT DOCUMENTS 805839  4/1974  Belgium .................. 260/239 BF

OTHER PUBLICATIONS

Gozzo et al., Carbamoyl Sulfoxides, A Logical Development of a Metabolic Investigation on the Thiolcarbamate Drepramon, Reports and Informations, Section III, Chemical Control, Part I, VIII International Plant Protection Congress, Moscow, 1975.
Tilles III, Chem. Abstracts, vol. 73, Abstract No. 55977m (1970).

*Primary Examiner*—Alton D. Rollins
*Attorney, Agent, or Firm*—Edwin H. Baker

[57] ABSTRACT

Herbicidal active sulfoxide and sulfone compounds and their method of use as described herein. The compounds have the following generic formula:

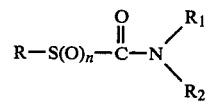

wherein n is 1 or 2; R is selected from the group consisting of lower alkyl and lower haloalkyl; $R_1$ and $R_2$ taken together form an alkylene group having 5 or 6 carbon atoms, alkyl substituted alkylene group or

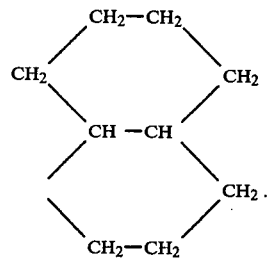

6 Claims, No Drawings

HERBICIDAL ACTIVE SULFOXIDE AND SULFONE COMPOUNDS

CROSS-REFERENCE TO RELATED APPLICATION

This is a continuation of application Ser. No. 567,910, filed Apr. 14, 1975, abandoned, which is a continuation-in-part of application Ser. No. 371,325, filed June 18, 1973, abandoned which is a continuation-in-part of application Ser. No. 280,385, filed Aug. 14, 1972, abandoned.

DESCRIPTION OF THE INVENTION

This invention is directed to a novel group of compounds which may be generally described as sulfoxide and sulfone derivatives of thiocarbamates which are highly active herbicides. The compounds of the present invention are represented by the generic formula:

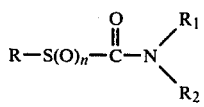

wherein n is 1 or 2; R is selected from the group consisting of lower alkyl having 1–6 carbon atoms and lower haloalkyl having 1–6 carbon atoms; $R_1$ and $R_2$ taken together form an alkylene group having 5 or 6 carbon atoms, alkyl having 1–4 carbon atoms substituted alkylene group having 5 or 6 carbon atoms or

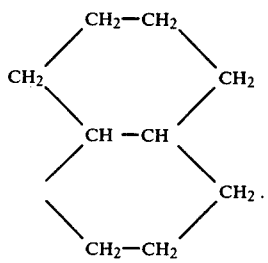

The above-noted compounds can be prepared by reacting an oxidizing agent such as peracetic acid or m-chloroperoxybenzoic acid with a thiocarbamate compound corresponding to the following formula:

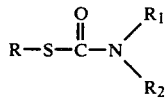

wherein R, $R_1$ and $R_2$ have been defined above. The reaction is carried out in the presence of a solvent such as chloroform, methylene chloride, benzene or toluene and at a reduced temperature of from about −25° C. to about 60° C. The amount of oxidizing agent used must be at least one molar equivalent to form the sulfoxide derivative and at least two molar equivalents to form the sulfone derivatives.

The thiocarbamate compounds are known herbicides and their method of synthesis is known; see U.S. Pat. Nos. 2,913,327, 2,983,747, 3,133,947, 3,175,897 and 3,185,720 for example. However, the use of these thiocarbamates as reactive intermediates to form other compounds that also have pesticidal activity is unexpected.

In order to illustrate the merits of the present invention, the following examples are provided:

EXAMPLE I

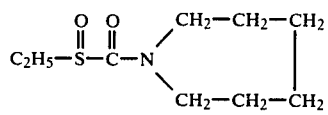

A solution was formed containing 11.2 grams (0.055 mole) of m-chloroperoxybenzoic acid and 200 cc. of methylene chloride in a reaction vessel. This solution was cooled in dry ice to −14° C. wherein 9.4 grams (0.05 mole) of S-ethylhexahydro-1H-azepine-1-carbothioate was added over a period of four minutes wherein the temperature increased to −13° C. The reaction mass was cooled to −14.5° C. and allowed to fluctuate for about 1 hour wherein the reaction mass was cooled to −5° C. Wherein the reaction mass was allowed to warm to 20° C. The reaction mass was then cooled to 2.5° C. wherein the mixture was filtered and the cake was washed with two portions of 25 cc. of methylene chloride. The combined filtrate was washed with four portions of 100 cc. 5 percent sodium carbonate solution and two portions of 100 cc. of water, dried over magnesium sulfate and concentrated in the rotary evaporator, first under water pump vacuum and finally under high vacuum to yield 9.1 grams of residual liquid. This residual liquid was redistilled to yield 8.0 grams of product, $n_D^{30}=1.5274$.

EXAMPLE II

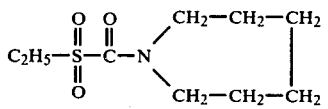

A solution was formed containing 22.3 grams (0.11 mole) of m-chloroperoxybenzoic acid in 300 cc. of methylene chloride in a reaction vessel. This solution was warmed to 29.5° C. wherein 9.4 grams of S-ethylhexahydro-1H-azepine-1-carbothioate was added over a period of three minutes. During the addition the temperature rose to 41° C. After 1.5 hours the solution was cooled to 9° C. and filtered with the cake being washed with two portions of 25 cc. of methylene chloride. The filtrate was washed with four portions of 100 cc. 5% solution of sodium carbonate and two portions of 100 cc. of water, dried over magnesium sulfate and concentrated in a rotary evaporator under water pump vacuum to yield 10.3 grams of product, $n_D^{30}=1.5000$.

EXAMPLE III

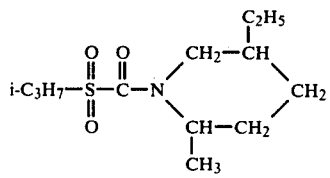

A solution was formed containing 22.3 grams (0.11 mole) of m-chloroperoxybenzoic acid in 300 cc. methylene chloride. This solution was cooled to 30.5° C. wherein 11.5 grams (0.05 mole) of S-isopropyl-5-ethyl-2-methylpiperidine-1-carbothioate was added over a period of 3 minutes. During the addition the temperature rose to 41.5° C. The reaction was maintained at this temperature and then cooled in ice and filtered with the cake being washed with two portions of 25 cc. of methylene chloride and dried in the oven. The combined filtrate was washed with four portions of 100 cc. 5% solution sodium carbonate and two portions of 100 cc. water, dried over magnesium sulfate and concentrated in the rotary evaporator, first under water pump vacuum and finally under high vacuum to yield 12.2 grams of product, $n_D^{30} = 1.4871$.

EXAMPLE IV

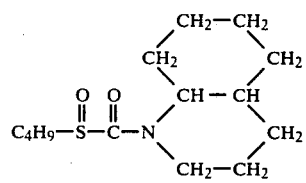

A solution was formed containing 12.8 grams of S-butyl decahydroquinoline-1-carbothioate (0.05 mole) in 200 cc. of methylene chloride. This solution was cooled to $-14°$ C. wherein 10.7 grams (0.0525 mole) of m-chloroperoxybenzoic acid was added over a period of 5 minutes. The reaction mass was maintained at this temperature for a period of about 1 hour and 10 minutes, wherein it was warmed to $-5°$ C. and maintained at this temperature for another 30 minutes. Thereafter, the reaction mass was allowed to warm to 16° C. wherein the mixture was filtered and the cake washed with two portions of 25 cc. of methylene chloride. The combined filtrate was washed with four portions of 100 cc. 5% sodium carbonate solution and two portions of 100 cc. water, dried over magnesium sulfate and concentrated in a rotary evaporator, first under water pump vacuum and finally under high vacuum to yield 12.0 grams of product, $n_D^{30} = 1.5282$.

Other compounds were prepared in an analogous manner starting with the appropriate starting materials as outlined above. The following is a table of compounds representative of those embodied by the present invention. Compound numbers have been assigned to them and are used for identification throughout the balance of the specification.

TABLE I $$R-S(O)_n-\underset{\underset{O}{\|}}{C}-N\underset{R_2}{\overset{R_1}{\diagup}}$$

| Compound Number | R | $R_1$ and $R_2$ | n |
|---|---|---|---|
| 1 | $-C_2H_5$ | 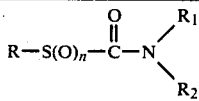 | 1 |
| 2 | $-C_2H_5$ | piperidine ring (CH2-CH2-CH2 / CH2-CH2-CH2) | 2 |
| 3 | n-$C_3H_7$ | pyrrolidine-type ring (CH2-CH2 / CH2 / CH2-CH2) | 1 |
| 4 | n-$C_3H_7$ | same ring as above | 2 |
| 5 | i-$C_3H_7$ | ring with $C_2H_5$ and $CH_3$ substituents | 1 |
| 6 | i-$C_3H_7$ | same ring as 5 | 2 |
| 7 | $-C_3H_6-Cl$ | ring with two $CH_3$ substituents | 1 |
| 8 | $-C_3H_6-Cl$ | same ring as 7 | 2 |
| 9 | n-$C_4H_9$ | decahydroquinoline ring | 1 |
| 10 | $-i-C_3H_7$ | (CH2-CH2-CH2 / CH2-CH2-CH2) | 1 |
| 11 | $-C_2H_5$ | ring with $CH_3$ substituent | 1 |

TABLE I-continued $$R-S(O)_n-\overset{\overset{O}{\|}}{C}-N\overset{R_1}{\underset{R_2}{\diagdown}}$$

| Compound Number | R | $R_1$ and $R_2$ | n |
|---|---|---|---|
| 12 | —n-C$_3$H$_7$ | (2-methylcyclohexyl ring: CH$_2$—CH$_2$, CH$_2$, CH—CH$_2$, CH$_3$) | 1 |
| 13 | —n-C$_3$H$_7$ | (piperidinyl: CH$_2$—CH$_2$—CH$_2$ / CH$_2$—CH$_2$—CH$_2$) | 1 |
| 14 | —n-C$_4$H$_9$ | (piperidinyl: CH$_2$—CH$_2$—CH$_2$ / CH$_2$—CH$_2$—CH$_2$) | 1 |
| 15 | —i-C$_4$H$_9$ | (piperidinyl: CH$_2$—CH$_2$—CH$_2$ / CH$_2$—CH$_2$—CH$_2$) | 1 |
| 16 | —n-C$_3$H$_6$—Cl | (2,5-diethylpyrrolidinyl: C$_2$H$_5$, CH$_2$—CH, CH$_2$, CH—CH$_2$, C$_2$H$_5$) | 1 |
| 17 | —C$_2$H$_5$ | (2,5-diethylpyrrolidinyl) | 1 |
| 18 | —CH$_3$ | (2-ethyl-5-methylpyrrolidinyl: C$_2$H$_5$, CH$_2$—CH, CH$_2$, CH—CH$_2$, CH$_3$) | 1 |
| 19 | —C$_2$H$_5$ | (2-ethyl-5-methylpyrrolidinyl) | 1 |
| 20 | —n-C$_3$H$_7$ | (2-ethyl-5-methylpyrrolidinyl) | 1 |
| 21 | —n-C$_4$H$_9$ | (2-ethyl-5-methylpyrrolidinyl) | 1 |
| 22 | —i-C$_4$H$_9$ | (2-ethyl-5-methylpyrrolidinyl) | 1 |
| 23 | —sec-C$_4$H$_9$ | (2-ethyl-5-methylpyrrolidinyl) | 1 |

HERBICIDAL SCREENING TESTS

As previously mentioned, the novel compounds herein described are phytotoxic compounds which are useful and valuable in controlling various plants species. Compounds of this invention are tested as herbicides in the following manner.

A. Preemergence Herbicide Screening Test

Using an analytical balance, 20 mg of the compound to be tested is weighed out on a piece of glassine weighing paper. The paper and compound are placed in a 30 ml wide-mouth bottle and 3 ml of acetone containing 1% Tween 20 ® is added to dissolve the compound. If the material is not soluble in acetone, another solvent such as water, alcohol or dimethylformamide (DMF) is used instead. When DMF is used, only 0.5 ml or less is used to dissolve the compound and then another solvent is used to make the volume up to 3 ml. The 3 ml of solution is sprayed uniformly on the soil contained in a small Styrofoam flat one day after planting weed seeds in the flat of soil. A No. 152 DeVilbiss atomizer is used to apply the spray using compressed air at a pressure of 5 lb/sq.in. The rate of application is 8 lb/acre and the spray volume is 143 gal/acre.

On the day preceding treatment, the Styrofoam flat which is 7 inches long, 5 inches wide and 2.75 inches deep is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), yellow foxtail (*Setaria glauca*), watergrass (*Echinochloa crusgalli*), red oat (*Avena sativa*), redroot pigweed (*Amaranthus retroflexus*), Indian mustard (*Brassica iuncea*) and curly dock (*Rumex crispus*). Ample seeds are planted to give about 20 to 50 seedlings per row after emergence depending on the size of the plants.

After treatment, the flats are placed in the greenhouse at a temperature of 70° to 85° F. and watered by sprinkling. Two weeks after treatment the degree of injury or control is determined by comparison with untreated check plants of the same age. The injury rating from 0 to 100% is recorded for each species as percent control with 0% representing no injury and 100% representing complete kill.

B. Postemergence Herbicide Screening Test

Seeds of six plant species, including hairy crabgrass, red oat, mustard, curly dock and Pinto beans (*Phaseolus vulgaris*) are planted in the Styrofoam flats as described above for preemergence screening. The flats are placed in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg of the test compound, dissolving it in 5 ml of acetone containing 1% Tween 20 ® and then adding 5 ml of water. The solution is sprayed on the foliage using a No. 152 DeVilbiss atomizer at an air pressure of 5 lb/sq. in. The spray concentration is 0.2% and the rate is 8 lb/acre. The spray volume is 476 gal/acre.

The results of these tests are shown in Table II.

TABLE II
HERBICIDAL ACTIVITY - SCREENING RESULTS

| Compound | Percent Control* at 8 lb/A | |
|---|---|---|
| Number | Preemergence | Postemergence |
| 1 | 91 | 65 |
| 2 | 0 | 26 |
| 3 | 91 | 68 |
| 4 | 0 | 69 |
| 5 | 99.9 | 77 |
| 6 | 0 | 65 |
| 7 | 99.7 | 74 |
| 8 | 0 | 67 |
| 9 | 99.7 | 83 |
| 10 | 92 | 83 |
| 11 | 99 | 71 |
| 12 | 99.7 | 79 |
| 13 | 95 | 74 |
| 14 | 100 | 78 |
| 15 | 99 | 79 |
| 16 | 98 | 89 |
| 17 | 98 | 78 |
| 18 | 93 | 71 |
| 19 | 99 | 82 |
| 20 | 100 | 83 |
| 21 | 100 | 82 |
| 22 | 30 | 0 |
| 23 | 100 | 70 |

*Average for seven plant species in the preemergence test and for six plant species in the postemergence test.

| Compound Number | Percent Control* at 20 lb/A Preemergence |
|---|---|
| 2 | 12 |

*Average for seven species.

The compounds of the present invention can be used in any convenient form. Thus, the compounds can be made into emulsifiable liquids, emulsifiable concentrates, liquids, wettable powders, powders, granular or any other convenient form, and applied to the soil to control the undesired vegetation. The amount of active ingredient used will vary depending on cost and desired results. In general, from about 1 to 50 lbs. per acre active ingredient is usually employed.

What is claimed is:

1. A compound represented by the following formula

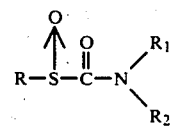

wherein R is lower alkyl having 1–4 carbon atoms or chloropropyl; $R_1$ and $R_2$ together with the nitrogen atom to which they are attached form piperidino, hexamethyleneimino, decahydroquinolino, 2,5-dimethylpiperidino, 5-ethyl-2-methylpiperidino.

2. The compound as set forth in claim 1 wherein R is —$C_2H_5$, and $R_1$ and $R_2$ are

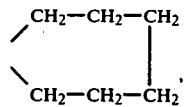

3. The compound as set forth in claim 1 wherein R is n—$C_3H_7$, and $R_1$ and $R_2$ are

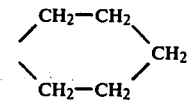

4. The compound as set forth in claim 1 wherein R is i—$C_3H_7$, and $R_1$ and $R_2$ are

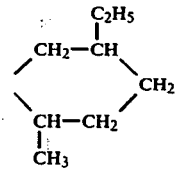

5. The compound as set forth in claim 1 wherein R is —$C_3H_6$—Cl, and $R_1$ and $R_2$ are

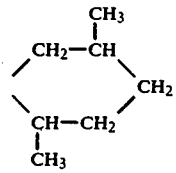

6. The compound as set forth in claim 1 wherein R is n—$C_4H_9$, and $R_1$ and $R_2$ are

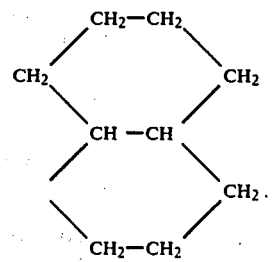

* * * * *